United States Patent [19]

Coates

[11] Patent Number: 5,045,704

[45] Date of Patent: Sep. 3, 1991

[54] METHOD FOR DETERMINING ABSOLUTE REFLECTANCE OF A MATERIAL IN THE ULTRAVIOLET RANGE

[75] Inventor: Vincent J. Coates, Palo Alto, Calif.

[73] Assignee: Nanometrics Incorporated, Sunnyvale, Calif.

[21] Appl. No.: 473,649

[22] Filed: Feb. 1, 1990

[51] Int. Cl.$^5$ .............................................. G01J 1/42
[52] U.S. Cl. ................... 250/372; 356/445; 356/448
[58] Field of Search ............... 250/372; 356/445, 448, 356/51

[56] References Cited

U.S. PATENT DOCUMENTS

| | | | |
|---|---|---|---|
| 4,035,085 | 7/1977 | Seiner | 356/448 |
| 4,455,090 | 6/1984 | Roberts | 356/448 |
| 4,575,252 | 3/1986 | Akiyama | 250/228 |

FOREIGN PATENT DOCUMENTS 0013438 1/1989 Japan ................................. 250/372

OTHER PUBLICATIONS

"Measurement and Analysis of Reflectance Spectra of SiP2", Applied Optics/vol. 11, No. 9 (Sep. 1972) John R. Barkley, pp. 1928-1935.

*Primary Examiner*—Carolyn E. Fields
*Assistant Examiner*—Drew A. Dunn
*Attorney, Agent, or Firm*—Linval B. Castle

[57] ABSTRACT

A method for determining a value of absolute reflectance of a material at a predetermined wavelength, in the ultraviolet range from its measured reflectance which includes system losses contributed by optics, illumination sources, detectors, etc. The method involves the measurement of reflectance from a known material such as single crystal silicon whose absolute reflectance is well known, dividing the measured value by the absolute value to obtain a system efficiency coefficient at the known wavelength and then, without changing the illumination or optics, measuring the reflectance of the unknown material and applying this coefficient to this measured value to obtain its absolute value.

5 Claims, 1 Drawing Sheet

METHOD FOR DETERMINING ABSOLUTE REFLECTANCE OF A MATERIAL IN THE ULTRAVIOLET RANGE

BRIEF SUMMARY OF THE INVENTION

This invention relates to the determination of reflectance from a material and particularly to the determination of absolute reflectance independent of losses in an associated optical system.

Some materials are transparent with very little incident energy being reflected from the surface and some materials are opaque and absorb nearly all incident energy and reflect very little. In many materials the ratio of incident energy to reflected energy, or reflectance, varies according to the wavelength of the incident radiation. For example, silicon as used in electronic microcircuits is transparent to infrared wavelengths, translucent between about one micron and infrared, and opaque to ultraviolet radiation.

It is often necessary to determine the energy absorption of some material with unknown chemical contents. An accurate value for absorption can easily be computed from a knowledge of the absolute reflectance from the unknown material since the incident energy can only be divided into absorption and reflectance. But a value for absolute reflectance is not readily obtainable since any measured value of reflectance at some predetermined wavelength is contaminated by losses contributed by the system optics, such as absorption of lenses, illumination sources, beamsplitters, gratings, detectors, etc., all of which also vary with wavelengths.

The object of this invention is to determine the absolute reflectance value of a test material at a desired wavelength, from a measured value of reflectance.

Briefly described, the method involves the steps of measuring the reflectance of a known material, such as single crystal silicon or aluminum specimen, at the desired wavelength, computing the value of absolute reflectance from absorption data available in myriads of handbooks, and then dividing the absolute value by the measured value to derive a product of all optical system coefficients. This value of the coefficients is stored. An unknown material is then tested with the same unchanged optical system and at the same wavelength to obtain a measured reflectance value which, when multiplied by the stored coefficient, yields the absolute reflectance value of the unknown material.

BRIEF DESCRIPTION OF THE DRAWINGS

In the drawings which illustrate the preferred embodiment of the invention.

DETAILED DESCRIPTION

Figure 1:
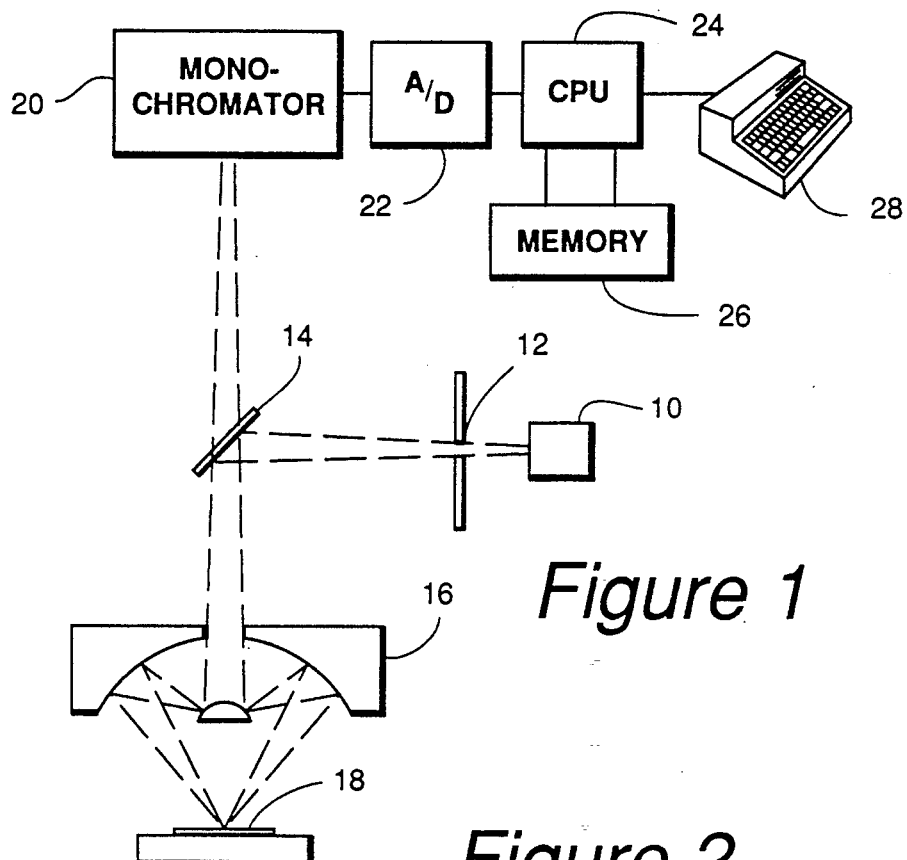
FIG. 1 is a schematic drawing illustrating a reflective microscope and detector processing apparatus for ultraviolet examinations.
Figure 2:
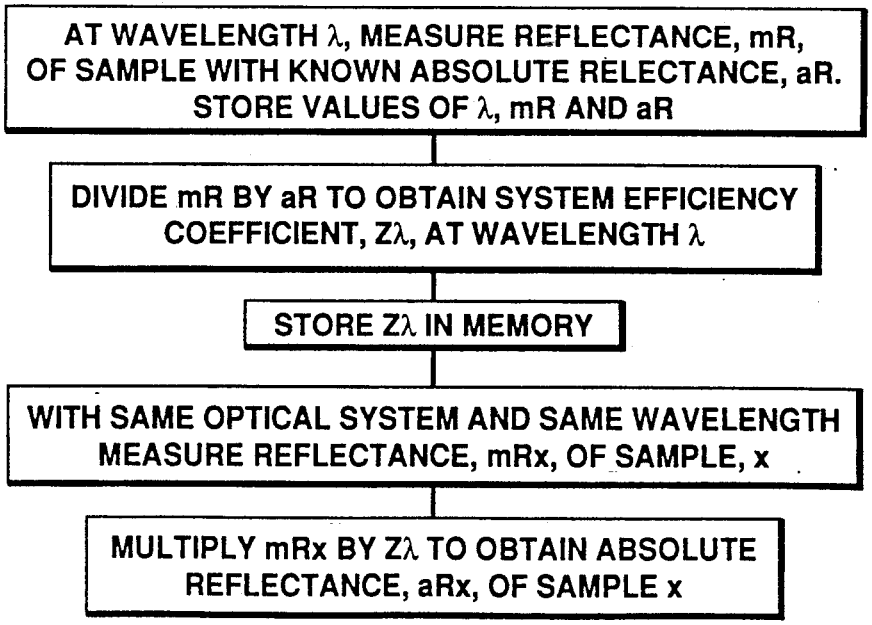
FIG. 2 illustrate the steps for determining absolute reflectance of an unknown material.

FIG. 1 illustrates a typical microscope for measuring reflectance in the ultraviolet range. Since the material used in the construction of typical refractive lenses is chromatic or opaque to UV radiation, only reflective optical devices may be used. Hence, a UV source 10 with known output energy, such as a deuterium discharge tube, with output beam condensed by a small iris 12 is reflected from a planar quartz beam splitter 14 into a reflective objective lens 16 which focuses the UV beam onto a specimen 18. The image from the specimen 18 is magnified by the reflective objective and, after passing through the planar quartz beam splitter 14, is focused into a monochromator 20 where the image beam is passed through a narrow slit to isolate a narrow band of wavelengths before detection.

The detected image beam, after being converted by an analog-to-digital converter 22, is applied to a computer 24 having a memory 26 and an input-output device 28, such as a keyboard terminal.

When the microscope system of FIG. 1 is used for measuring reflectances, all optical elements such as the beam splitter 14, the several reflective surfaces of the objective lens 16 and the internal optical elements in the monochromator 20, absorb energy from the incident radiating beam of the source 10. Further, the absorbed energy varies with variations in the incident wavelength.

A value of reflectance can easily be measured with the microscope system, but that is a measured reflectance, mR, which has little value since it includes the unknown system losses resulting from the energy absorption of the optical elements. The type of reflectance of value is the absolute reflectance, aR. the ratio of reflected energy to incident energy, independent of system losses.

Absolute reflectance of an unknown material can be determined if one knows the values of both absolute and measured reflectance of a known material at the desired wavelength. With this data, the system losses, or system efficiency coefficient, $Z\lambda$, at wavelength $\lambda$, is computed by merely dividing the measured value by the absolute value of reflectance. Many reference books list tables of refractive index and absorption of various materials at various frequencies and many also list the values of absolute reflectance at various wavelengths. Thus, absolute reflectance values, aR, are available or calculable for several pure materials, such as single crystal silicon.

With knowledge of an absolute reflectance value, aR, of a particular pure material at some known wavelength $\lambda$, the system efficiency coefficient, $Z\lambda$ at that wavelength, is determined by measuring the measured reflectance, mR, and divide by aR:

$$Z\lambda = mR/aR \quad (1)$$

To determine the absolute reflectance, aRx, of a material, x, measure the measured reflectance, mRx, of that unknown material, x, at the same wavelength, $\lambda$, and with the same optical system, and multiply the results by the system efficiency coefficient, $Z\lambda$.

$$aRx = mRx(Z\lambda) \quad (2)$$

The determination of absolute reflectance can readily be performed by the computer system illustrated in FIG. 1. The value aR of the known material at the predetermined wavelength is entered through the keyboard 28 into the computer 24 which is programmed to perform the simple division and multiplication shown in Equations (1) and (2) above. The value, aR is stored in the memory 26. The reflectance, mR is then measured of the known material 18 on the microscope stage and the detected value is stored into the memory 26. The computer 24 then performs Equation (1) and stores the efficiency coefficient, $Z\lambda$ in memory. Without making any changes in the energy source or the optical system, the known material 18 is replaced with the unknown material, x, and the reflectivity is measured to obtain the value, mRx, which is applied to the computer 24 along with the efficiency coefficient Zλ, in memory. The computer performs the multiplication of Equation (2) to obtain the absolute reflectance, aRx of the unknown material, x.

I claim:

1. A method for determining an absolute reflectance of material from a microscopic measurement of its measured reflectance in the ultraviolet radiation range, said method comprising the steps of:

determining a value of absolute reflectance of a known material at a predetermined wavelength;

measuring the reflectance of said known material to obtain a value of measured reflectance with a microscope illuminated with radiation at said predetermined wavelength;

with said values of absolute reflectance and measured reflectance, calculating an efficiency coefficient representing all absorption and losses caused by the microscope optical system, its reflectance detectors and its illumination system at said predetermined wavelength;

measuring the reflectance of an unknown material to obtain a second value of measured reflectance with said microscope illuminated with said radiation at said predetermined wavelength;

applying said efficiency coefficient to said second value of measured reflectance to obtain a value of absolute reflectance of said unknown material.

2. The method claimed in claim 1 wherein said step of applying includes the step of multiplying said second value by said efficiency coefficient.

3. The method claimed in claim 2 wherein said microscope is a reflecting microscope.

4. The method claimed in claim 3 wherein said predetermined wavelength is in the ultraviolet radiation range.

5. The method claimed in claim 2 wherein the determined values of absolute reflectance of said known material, said value of measured reflectance of said known material and said value of measured reflectance of said unknown material are stored in a memory of a computer that performs the step of calculating said efficiency coefficient and said value of absolute reflectance of said unknown material.

* * * * *